(12) United States Patent
Wei et al.

(10) Patent No.: US 6,741,359 B2
(45) Date of Patent: May 25, 2004

(54) OPTICAL COHERENCE TOMOGRAPHY OPTICAL SCANNER

(75) Inventors: Jay Wei, Fremont, CA (US); Yonghua Zhao, Dublin, CA (US); James P. Foley, Fremont, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 153 days.

(21) Appl. No.: 10/153,297

(22) Filed: May 22, 2002

(65) Prior Publication Data

US 2003/0218755 A1 Nov. 27, 2003

(51) Int. Cl.[7] .......................... G01B 9/02; G02B 26/08; A61B 3/10
(52) U.S. Cl. .......................... 356/512; 351/221; 359/196
(58) Field of Search .................. 356/489, 495, 356/511, 512; 351/243, 221; 359/196

(56) References Cited

U.S. PATENT DOCUMENTS

| 5,321,501 A | * | 6/1994 | Swanson et al. ............ 356/479 |
| 5,329,322 A | * | 7/1994 | Yancey ....................... 351/211 |
| 5,493,109 A | * | 2/1996 | Wei et al. ................. 250/201.3 |

OTHER PUBLICATIONS

"Lens Design Fundamentals" by R. Kingslake, Academic Press, 1978, pp. 87, 194–196, 208, 236, 268.
"Optical Coherence Tomography of Ocular Diseases" by C.A. Puliafito et al. ALACK Incorporated, 1996, p. 14.

* cited by examiner

Primary Examiner—Frank G. Font
Assistant Examiner—Patrick Connolly
(74) Attorney, Agent, or Firm—Michael B. Einschlag

(57) ABSTRACT

One embodiment of the present invention is a scanner for a beam of scanning optical coherence tomography ("OCT") radiation that includes: (a) a source of OCT radiation; (b) a scanner; and (c) scanning optics whose image surface has a negative field curvature.

15 Claims, 5 Drawing Sheets

US 6,741,359 B2

OPTICAL COHERENCE TOMOGRAPHY OPTICAL SCANNER

TECHNICAL FIELD OF THE INVENTION

One or more embodiments of the present invention relate to methods and apparatus for performing optical scans. In particular, one or more embodiments of the present invention relate to method and apparatus for performing an optical coherence tomography ("OCT") optical scan to image, for example, and without limitation, tissue and anatomical features of an eye.

BACKGROUND OF THE INVENTION

An optical coherence tomography ("OCT") apparatus (for example, like one disclosed in U.S. Pat. No. 5,321,501) is an optical imaging apparatus that can perform micron-resolution, cross-sectional imaging of biological tissue. As is well known, the quality of an OCT image depends on: (a) the resolution of the image (which resolution is related to the coherence length of a radiation source used in the OCT apparatus); and (b) the signal-to-noise ratio of the OCT image.

To increase the signal-to-noise ratio of the OCT image, scanning optics is optimized for a particular application so that a maximum amount of reflected or scattered OCT radiation can be collected by the scanning optics. Such optimization is important for scanning anterior segments of features of an eye such as, for example, an anterior surface of the cornea, because the curvature of, for example, the anterior corneal surface is steep, and much of the reflected OCT radiation is therefore directed away from an optical axis along which the reflected OCT radiation is collected.

A book entitled "Optical Coherence Tomography of Ocular Diseases" by C. A. Puliafito et al, published by SLACK Incorporated, 1996, at p. 14 discloses scanning optics for use in imaging anterior segments of features of the eye. As shown in FIGS. 1–12 thereof, the scanning optics is a telecentric optical system that causes a beam of scanning OCT radiation to be parallel at various positions across the front of the eye. The disclosed scanning optics is problematic in such applications because the curvature of, for example, the anterior corneal surface is steep, and as a result, much of the reflected OCT radiation is lost. Consequently, a detected signal produced by such reflected OCT radiation is weak outside a small central section of the corneal surface.

This issue is addressed in U.S. Pat. No. 5,493,109 to J. Wei et al. which discloses scanning optics that causes chief rays of the scanning OCT radiation to be focused at a center of the cornea. As a result, the scanning OCT radiation is directed to impinge substantially perpendicular to the anterior corneal surface, and as a result, a maximum reflected signal is acquired.

However, the scanning optics disclosed in both of the above-referenced prior art references is problematic in that it traces out a scanning image over an inward curved surface, i.e., a surface whose curvature is opposite that of the anterior corneal surface. In particular, a point of best focus of the scanning beam (as it is scanned over the anterior corneal surface) lies on a curved surface whose curvature is opposite to the curvature of the anterior corneal surface.

In addition to the above, using prior art OCT apparatus, OCT longitudinal scans into the eye over depths larger than the thickness of the cornea are problematic. This is because the beam of scanning OCT radiation may be out of focus when the longitudinal scan depth extends deep into the eye. Hence, the detected signal strength will not be the same when the beam of scanning OCT radiation is scanned at different longitudinal depths into the eye. To overcome this problem, the width of the beam of scanning OCT radiation is designed to be small enough that the depth of focus of the beam is comparable to the longitudinal scan depth range required for a particular application. However, this causes a problem because reducing the width of the beam of scanning OCT radiation is equivalent to reducing the numerical aperture ("N.A.") of the scanning optics. This, in turn, reduces the radiation collection efficiency of the scanning optics for reflected or scattered OCT radiation. For example, as is well known, radiation collection efficiency is proportional to the $2^{nd}$ power of N.A. of the scanning optics, and depth of focus is inversely proportional to the $2^{nd}$ power of N.A. As a result, the radiation collection efficiency of the scanning optics for reflected or scattered OCT radiation is proportional to the inverse of the longitudinal scan depth range. In addition, the problem is even worse when the point of best focus of the beam of scanning OCT radiation traces out a curved surface that is opposite to a desired scanning beam image geometry (i.e., for example, that of the geometry of the anterior corneal surface).

In light of the above, there is a need in the art for method and apparatus to solve one or more of the above-identified problems.

SUMMARY OF THE INVENTION

One or more embodiments of the present invention advantageously satisfy one or more of the above-identified problems. Specifically, one embodiment of the present invention is a scanner for a beam of scanning optical coherence tomography ("OCT") radiation that comprises: (a) a source of OCT radiation; (b) a scanner; and (c) scanning optics whose image surface has a negative field curvature.

DETAILED DESCRIPTION

Figure 1:
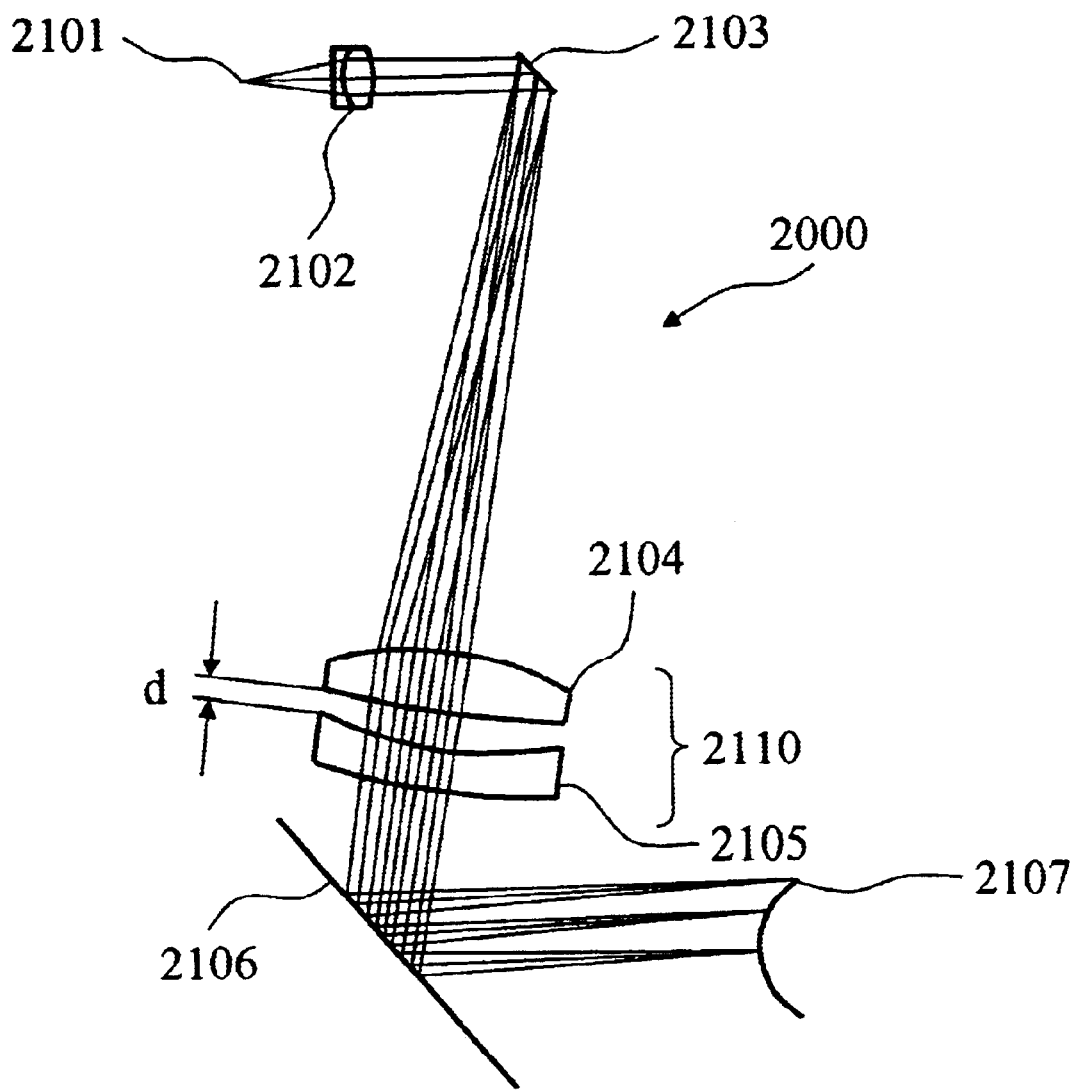
FIG. 1 shows, in pictorial form, a scanning optics system that is fabricated in accordance with one or more embodiments of present invention.

FIG. 1 shows, in pictorial form, scanning optics system 2000 that is fabricated in accordance with one or more embodiments of the present invention. In accordance with one such embodiment of the present invention, scanning optics system 2000 can be used, for example, and without limitation, in fabricating an optical coherence tomography assisted ("OCT-assisted"), ophthalmologic microscope as will be described below in conjunction with FIG. 2. In accordance with one such embodiment of scanning optics 2000, scanning optics system 2000 is designed to scan or image anterior segments of features of an eye. As such, it is designed so that its image surface (characterized, for example, by its field curvature or radius of curvature) can be configured to closely resemble the shape of anterior segments of features of the eye. As a result, for example, and without limitation, at least most of the anterior corneal surface, the sclera, and the iris of the eye can be sharply focused.

As shown in FIG. 1, "sample arm" optical fiber tip 2101 of an OCT apparatus (to be described in detail below in conjunction with FIG. 3) is located at a back focal plane of collimator lens system 2102 (as one of ordinary skill in the art can readily appreciate, lens system 2102 can be fabricated using one or more lens elements). It should be understood that embodiments of the present invention are not limited to use of a fiber optic embodiment of an OCT apparatus, and that further embodiments of the present invention include any one of a number of methods for fabricating OCT apparatus that are well known to those of ordinary skill in the art.

As further shown in FIG. 1, the beam of scanning OCT radiation output from optical fiber tip 2101 is collimated in the space between collimator lens system 2102 and scanner mirror 2103. As is well known, scanner mirror 2103 is driven by a scanner mechanism. Scanner mirror 2103 and the scanner mechanism can be fabricated in accordance with any one of a number of methods that are well known to those of ordinary skill in the art. For example, the scanner mechanism can be fabricated using, for example, and without limitation, a galvanometer, a step motor, a voice coil motor, and so forth. As is also well known, scanner mirror 2103 typically comprises two mirrors to scan the beam of scanning OCT radiation over a plane, however, scanner mirror 2103 is shown as a single mirror in FIG. 1 for ease of understanding the principles of the present invention.

The scanned, collimated beam output from scanner mirror 2103: (a) is focused at eye 2107 by scanning optics system 2110 (which is comprised of separated lens elements 2104 and 2105); and (b) is directed to eye 2107 by beamdirector 2106. Scanning mirror 2103 is located at a back focal plane of scanning optics system 2110 so that the axes of the beams of scanning OCT radiation are parallel in front of eye 2107. In addition, beamdirector 2106 reflects radiation at wavelengths included in the beam of scanning OCT radiation, and is used for convenience to fold the optics and reduce its size.

In accordance with one embodiment of the present invention, lens element 2104 is a positive lens element, and lens element 2105 is a negative lens element. Further, in accordance with one or more embodiments of the present invention, the magnitude of the power of negative lens element 2105 is larger than the magnitude of the power of positive lens element 2104. As a result, the image surface of scanning lens system 2110 is outwardly curved.

As is well known from geometrical optics, the radius of curvature of the image (i.e., the field curvature) of an optical system comprised of thin lens elements is inversely proportional to the Petzval sum. For an optical system comprised of several widely spaced thin elements, the Petzval sum is given by:

$$Ptz = \Sigma \phi_i \quad (1)$$

where $\phi$ is the power of a thin lens element, i.e., $\phi$ equals the inverse of the product of the focal length (f) of the thin lens element and the refractive index of the thin lens element (n), i.e., $\phi = 1/(nf)$.

If a positive singlet lens element is used to fabricate scanning optics system 2000, the field curvature of the image surface of scanning optics system 2000 (i.e., the curvature of the surface of best focus of the beam of scanning OCT radiation) will be curved inward (for example, curved opposite from the curvature of the anterior corneal surface), and the field curvature will be inversely proportional to the power of the singlet lens element.

However, if multiple lens elements are used to fabricate scanning optics system 2000, the total power cannot be determined by merely adding the powers of each lens element because the ray intercept at each lens element varies with the separation between the lens elements. For example, for an optics system comprised of two thin lens elements separated by distance d, the combined power can be written as:

$$\phi = \phi_1 + \phi_2 - d\phi_1\phi_2 \quad (2)$$

In accordance with one or more embodiments of the present invention, one can utilize various combinations of $\phi_1$ and $\phi_2$ to fabricate a scanning optics system having a desired power $\phi$ by adjusting the value of d. For example, assume that a scanning optics system comprises a positive lens element having power $\phi_1$ and a negative lens element having power $\phi_2$. Then, one can adjust d to obtain a desired value of combined power 100 according to eqn. 2. For example, as one can see from eqn. 2, the larger the value of d, the more negative $\phi_2$ can be, while $\phi$ still has a positive value.

In addition, as one can see by referring to eqn. 1, the field curvature of the image surface of the scanning optics system can be reduced by choosing a lens element having a large negative power $\phi_2$. Further, as seen from eqn. 1, if $\phi_2$ is negative and the magnitudes of $\phi_1$ and $\phi_2$ are equal, then the field curvature of the image surface of the scanning optics system will be zero. Finally, as seen from eqn. 1, if $\phi_2$ is negative and the magnitude of $\phi_2$ is larger than $\phi_1$, then the field curvature of the combination changes sign, and the image surface becomes outwardly curved. In fact, in accordance with one or more embodiments of the present invention, the image surface is outwardly curved so that it resembles the shape of anterior segments of features of the eye so that at least most of the anterior corneal surface, the sclera, and the iris of the eye are sharply focused.

In accordance with one or more embodiments of the present invention, the image surface of scanning lens system 2110 can be made outwardly curved so that it resembles the shape of, for example, the anterior corneal surface by adjusting distance d between lens elements 2104 and 2105. As a result, in accordance with such embodiments of the present invention, the best focus of the beam of scanning OCT radiation will be on the anterior corneal surface, the sclera, and the root of the iris. Advantageously, as a result of this, the numerical aperture ("N.A.") of scanning optics system 2110 can be increased to collect more of the scanning OCT radiation reflected and scattered from eye tissues.

In accordance with one or more embodiments of the present invention, the shape and material of lens elements 2104 and 2105, and gap distance d can be fabricated in many different combinations to satisfy particular design requirements. For example, in accordance with one such embodiment, lens elements 2104 and 2105 may be fabricated from different types of materials (for example, one may be fabricated from a flint glass, and the other may be fabricated from a crown glass) to compensate for dispersion of one glass with respect to wavelength, i.e., to correct for chromatic aberration. In addition, the shape of lens elements 2104 and 2105 can be designed to correct for optical aberrations such as spherical aberration, astigmatism, and coma. In further addition, lens elements 2104 and 2105 can also be designed as an achromat in a form known as a dialyte that is well known to those of ordinary skill in the art. In particular, in accordance with one such embodiment, a distance between scanning lens system 2110 and scanning mirror 2103 is about one focal length of the air spaced doublet (for example, a dialyte) so that the beams of scanning OCT radiation are parallel in front of eye 2107.

Although embodiments of the present invention have been described wherein a scanning lens system comprises two spaced-apart lens elements, those of ordinary skill in the art should readily appreciate that the present invention is not limited to such embodiments, and in fact, further embodiments exist wherein the scanning lens system comprises three or more spaced-apart lens elements.

Figure 2:
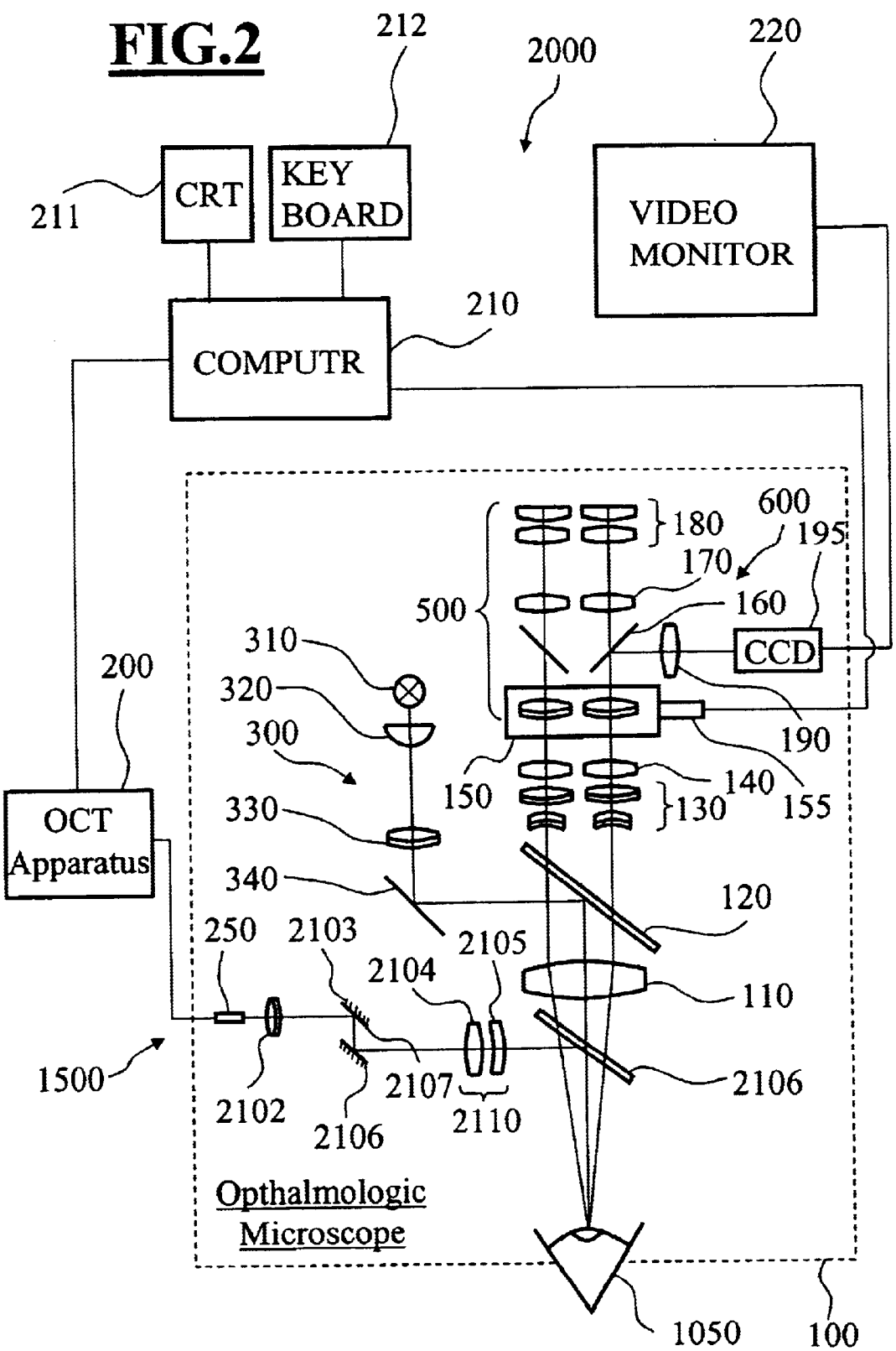
FIG. 2 shows, in pictorial form, an ophthalmologic microscope and an optical coherence tomography ("OCT") apparatus together with a scanning optics system that is fabricated in accordance with one or more embodiments of the present invention.

FIG. 2 shows, in pictorial form, ophthalmologic apparatus 1500 that comprises ophthalmologic microscope 100, OCT apparatus 200, and a scanning optics system that is fabricated in accordance with one embodiment of the present invention. As shown in FIG. 2, ophthalmologic microscope 100 includes objective lens 110 which may have a long working distance (~200 mm) for focusing on patient's eye 1050 during a procedure or an examination. Beamdirector 120 directs illumination radiation output from illumination source 310 from illumination path 300 toward objective lens 110. As shown in FIG. 2, beamdirector 120 is beamsplitter.

As further shown in FIG. 2, ophthalmologic microscope 100 further comprises optical magnification changer 130 which is set to a condition suitable for performing a particular procedure or examination (typically there are a number of groups of lenses arranged on a drum for providing varying magnifications such as, for example, 5×, 12×, 20×, and so forth). Radiation impinging upon optical magnification changer 130 is collimated by objective lens 110.

As further shown in FIG. 2, ophthalmologic microscope 100 further comprises: (a) relay lenses 140 which take collimated radiation output from optical magnification changer 130, and form an intermediate image of an object, for example, eye 1050; and (b) internal focusing lenses 150 which are used to focus on the intermediate image of the object formed by relay lenses 140, and provide a collimated beam (internal focusing lenses 150 move up and down along viewing path 500 to provide an opportunity for internal focus adjustment).

As further shown in FIG. 2, after passing through internal focusing lenses 150, radiation is collimated, and beamsplitter 160 couples a portion of the collimated radiation into optical path 600 to obtain a video image. The video image is obtained by use of video lens 190, CCD camera 195, and video monitor 220. As those of ordinary skill in the art can readily appreciate, although the use of a single CCD camera is shown, it is within the spirit of the present invention that embodiments may be fabricated utilizing two beamsplitters, i.e., beamsplitter 160 and a similarly placed beamsplitter, to provide stereoscopic viewing through two CCD cameras.

As further shown in FIG. 2, tube lenses 170 focus collimated radiation passed through beamsplitters 160 at an object plane of eye pieces 180. Eye pieces 180 then provide collimated output which is focused by a viewer's eyes. Since the above-described viewing path 500 is binocular, stereoscopic viewing can be obtained.

As further shown in FIG. 2, illumination path 300 is comprised of: (a) light source 310 (for example, and without limitation, an incandescent light source); (b) condenser lens 320 for collecting radiation output from light source 310; and (c) image lens 330 for filling the entrance pupil of objective lens 110 with the filament of incandescent light source 310.

Figure 3:
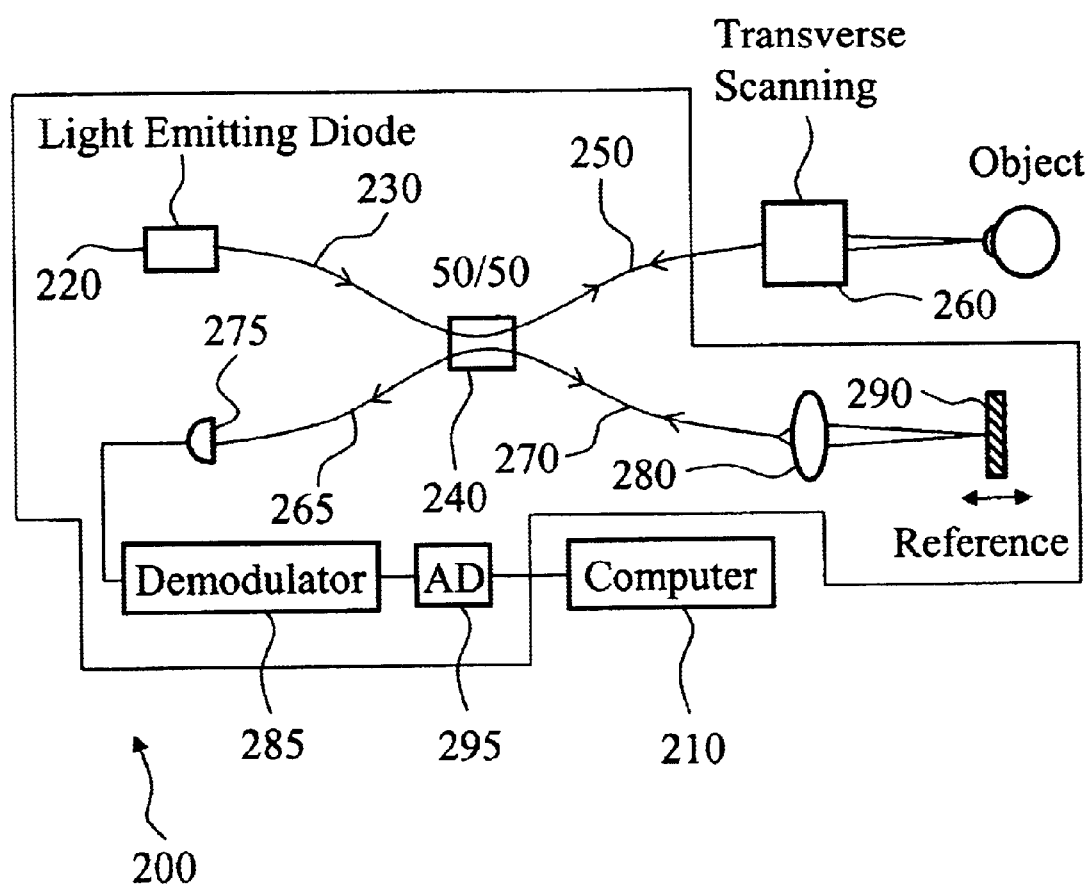
FIG. 3 shows, in pictorial form, a fiber optic embodiment of the OCT apparatus shown in FIG. 2.

FIG. 3 shows, in pictorial form, a fiber optic embodiment of an OCT apparatus that includes OCT apparatus 200 in a dark outline. As shown in FIG. 3, OCT apparatus 200 comprises CW radiation source 220, for example, and without limitation, a superluminescent laser diode having an output centered, for example, and without limitation, substantially at 850 nm. Output from source 220 is coupled into optical fiber 230, and is separated into two beams by 50/50 coupler 240. The output from 50/50 coupler 240 is coupled into optical fibers 250 and 270, respectively. The output from fiber 270 is imaged by lens system 280 onto reference mirror 290, and output from fiber 250 is directed to a transverse scanning mechanism (shown as transverse scanning mechanism 260 in FIG. 3). The output from the transverse scanning mechanism (for example, transverse scanning mechanism 260 in FIG. 3) is directed to impinge upon an object in a manner to be described in detail below. Then, radiation reflected from the object: (a) is coupled back into fiber 250; and (b) is superimposed by 50/50 coupler 240 with radiation that is reflected from reference mirror 290 and coupled back into fiber 270. Superimposed radiation output from 50/50 coupler 240 is coupled into fiber 265. As is known, there is interference between radiation reflected from the object and radiation reflected from reference mirror 290 if the optical path difference is smaller than the coherence length of radiation source 220. Reference mirror 290 is moved with a substantially constant velocity by means which are well known to those of ordinary skill in the art (not shown) and, as a result, the interference is detected as a periodic variation of a detector signal obtained by photodetector 275, the periodic variation having a frequency equal to a Doppler shift frequency which is introduced by moving reference mirror 290 with the constant velocity. The output from photodetector 275 is demodulated by demodulator 285, the demodulated output from demodulator 285 is converted to a digital signal by analog-to-digital converter 295 (A/D 295), and the output from A/D 295 is applied as input to computer 210 for analysis, for example, a personal computer. The interference signal vanishes as soon as the optical path difference between radiation reflected from the object and radiation reflected from reference mirror 290 becomes larger than the coherence length of source 220.

It should be understood that embodiments of the present invention are not limited to use of a fiber optic embodiment of an OCT apparatus described above in conjunction with FIG. 3, and that further embodiments of the present invention include any one of a number of methods for fabricating OCT apparatus that are well known to those of ordinary skill in the art. In addition, it should be understood that embodiments of the present invention are not limited to use of a translating reference mirror to provide depth scanning, and that further embodiments of the present invention include any one or a number of methods for providing longitudinal depth scanning that are well known to those of ordinary skill in the art.

Returning now to FIG. 2, output from OCT apparatus 200 (specifically output from fiber 250) is collimated by collimator lens system 2102 (a fiber tip of fiber 250 is located at a back focal plane of collimator lens system 2102), and is directed to scanner 2107 which is comprised of scanner mirrors 2103 and 2106, respectively. Scanner mirrors 2103 and 2106 are scanned, in response to input from computer 210, for example, and without limitation, to provide a predetermined scanning pattern in a plane in accordance with any one or a number of methods that are well known to those of ordinary skill in the art. The collimated beam output from scanner 2107 is focused at eye 1050 by scanning optics system 2110 comprised of separated lens elements 2104 and 2105, and is directed to eye 1050 by beamdirector 2106. As described above, in conjunction with the embodiment shown in FIG. 3, the beam of scanning OCT radiation has a wavelength centered at about 850 nm, and beamdirector 2106 comprises a dichroic coating so that scanning OCT radiation is reflected, and radiation from illumination path 300 passes through to enable viewing of eye 1050 using ophthalmologic microscope 100.

In accordance with one or more embodiments of the present invention, scanning mirrors 2103 and 2106 are orthogonally mounted, galvanometer driven scanning mirrors which are mounted on a pair of scanning motors (not shown), which scanning motors are operated under the control of computer 210 in a manner which is well known to those of ordinary skill in the art. In accordance with such embodiments, scanning mirrors 2103 and 2106 are located close to the back focus of scanning lens system 2110.

Computer 210 may position internal focusing lenses 150 (by sending an appropriate signal to motor 155) so that the corresponding focal plane of ophthalmologic microscope 100, depending on the position of internal focusing lenses 150, is at a predetermined position identified with a particular procedure or examination.

In accordance with one or more embodiments of the present invention, OCT unit 200 and scanning mirrors 2103 and 2106, in accordance with instructions from computer 210, provide raster, transverse OCT scans of, for example, anterior segments of features of eye 1050 in conjunction with a longitudinal OCT scan, all in a manner known in the art. The results are analyzed by computer 210 to obtain measurements such as: (a) an anterior corneal surface contour, (b) an anterior surface contour of the iris, and (c) an anterior surface contour of the lens. These data may be used, for example, and without limitation, to provide on-line monitoring of surgery. For example, output from computer 210 may be displayed on CRT 211 wherein various features obtained by the OCT longitudinal scan are made apparent by a display, for example, of signal strength as a function of location. Then, user input to computer 210 by means, for example, of keyboard 212 and/or a mouse (not shown), may be used to specify a range of locations of the longitudinal scan to use for auto-focusing. In response to the user input, computer 210 may choose a location which produces a signal strength maximum within a specified range of locations, and may determine an appropriate position of internal focusing lens 150 to achieve proper focus on the location providing the signal strength maximum. Then, computer 210 may send an appropriate signal to motor 155 to move internal focusing lens 150 to the appropriate position.

In one such embodiment of the present invention, thresholds are input to computer 210 for the purpose of identifying signal maxima corresponding to predetermined surfaces in the chamber of eye 1050. Then, computer 210 makes a correspondence between signals having levels above the maxima with the predetermined surfaces, and captures the spatial coordinates of the surfaces in space from the longitudinal scan position and from the position of the beam of scanning OCT radiation in the raster scan.

Figure 4:
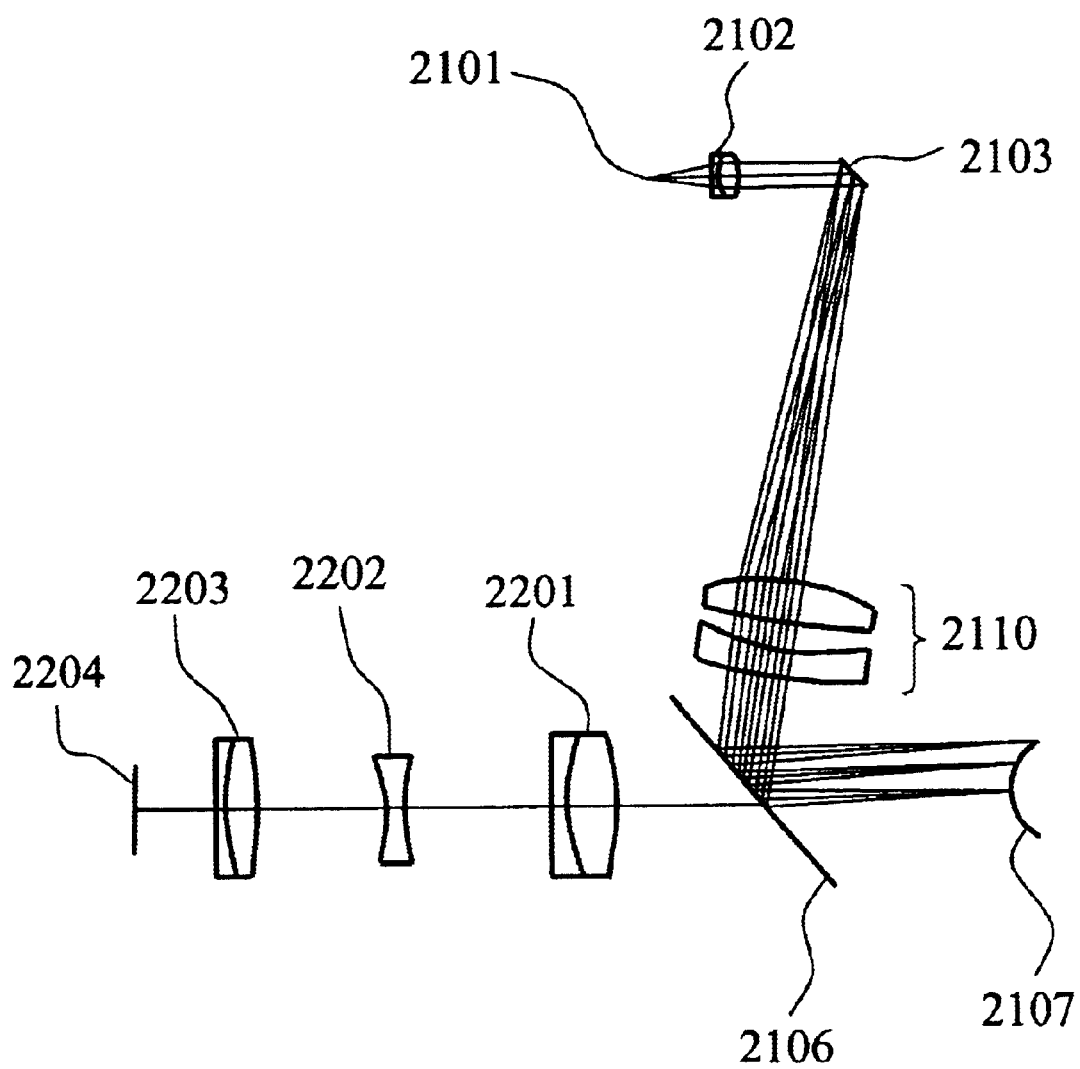
FIG. 4 shows, in pictorial form, the scanning optics system shown in FIG. 1 in conjunction with an optometer that is fabricated in accordance with one or more embodiments of the present invention.

FIG. 4 shows, in pictorial form, scanning optics system 2000 shown in FIG. 1 in conjunction with an optometer that is fabricated in accordance with one embodiment of the present invention. In accordance with this embodiment of the present invention, and as shown in FIG. 4, a visual object such as, for example, and without limitation, a picture is located at plane 2204, where plane 2204 is substantially in the back focal plane of target lens system 2203 (as one of ordinary skill in the art can readily appreciate, target lens system 2203 can be fabricated using one or more lens elements). In one such embodiment, the visual object is backlit using any type of source that is well known to those of ordinary skill in the art that produces light that passes through beamsplitter 2106. As further shown in FIG. 4, lens system 2202 is a negative lens system (as one of ordinary skill in the art can readily appreciate, lens system 2202 can be fabricated using one or more lens elements) that forms a virtual image of the visual object at its focal plane. Lastly, as still further shown in FIG. 4, the visual object is collimated by lens system 2201 (as one of ordinary skill in the art can readily appreciate, target lens system 2201 can be fabricated using one or more lens elements), and a real image is formed on the retina of eye.

In accordance with this embodiment, by moving or adjusting a position of negative lens system 2202 along an optic axis of the optometer, the real image of the visual object can be located in front of, or behind, the retina. Any one of a number of mechanisms that are well to those of ordinary skill in the art can be used to move negative lens system 2202, including, for example, and without limitation, motors, and/or screw mechanisms. Thus, in order for a patient to see the visual object clearly, he/she may have to accommodate his/her eye. As a result, the crystal lens of eye 2107 will change its position during the accommodation process. Hence, by moving the real image of the visual object during, for example, an OCT scan, one can study the anatomy of eye 2107 during the accommodation process. Further, by placing the pupil of eye 2107 substantially at the front focal plane of lens system 2201, one will obtain a telecentric system. This means that the size of the visual object will remain the same for all states of accommodation.

Figure 5:
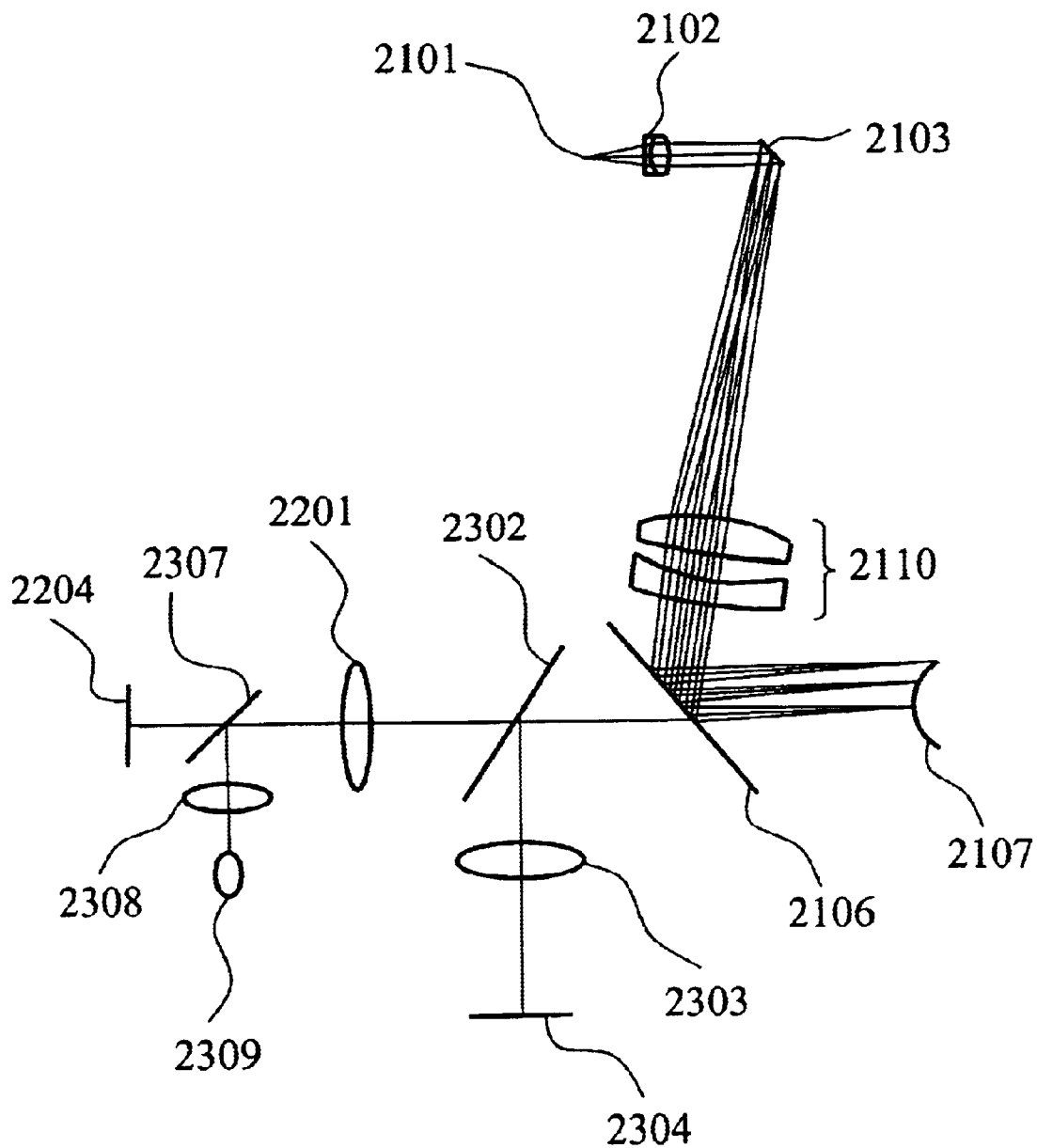
FIG. 5 shows, in pictorial form, the scanning optics system shown in FIG. 1 in conjunction with an optometer that is fabricated in accordance with one or more alternative embodiments of the present invention.

FIG. 5 shows, in pictorial form, scanning optics system 2000 shown in FIG. 1 in conjunction with an optometer that is fabricated in accordance with an alternative embodiment of the present invention. In accordance with this alternative embodiment, target lens system 2203 and negative lens system 2202 shown in FIG. 4 are removed, and a position of the visual object itself is moved or adjusted along an optic axis of the optometer to force eye 2107 to accommodate. In accordance with one or more such embodiments, the visual object is backlit using any type of source that is well known to those of ordinary skill in the art that produces light that passes through beamsplitter 2106.

Any one of a number of mechanisms are well to those of ordinary skill in the art can be used to move the visual object, including, for example, and without limitation, motors, and/or screw mechanisms. Then, in order for a patient to see the visual object clearly, he/she may have to have to accommodate his/her eye. As a result, the crystal lens of eye 2107 will change its position during the accommodation process.

As further shown in FIG. 5, a video path is inserted in the optical system for viewing eye 2107. In particular, radiation source 2309 (such as, for example, and without limitation, an LED, a lamp, and so forth) outputs radiation (preferably radiation that is not detected by the patent such as, for example, infrared radiation) that is imaged to the corneal plane of eye 2107 through lens system 2308, beamsplitter 2307, and lens system 2201. Radiation output from radiation source 2309 that is reflected by eye 2107 is directed by beamsplitter 2302 towards video lens system 2303 which forms a real image of eye 2107 on CCD sensor 2304 (as one of ordinary skill in the art can readily appreciate, lens system 2308 and video lens system 2303 can each be fabricated using one or more lens elements). In accordance with this embodiment of the present invention, the optical axis of the optometer is aligned with the optical path between the visual object and eye 2107. Hence, the optical axis of the optometer is aligned with the visual axis of eye 2107. As is well known, in certain clinical applications, for example, in determining a map of corneal thickness, it is important to do so relative to the visual axis of eye 2107. By observing a reflection of radiation output from source 2309 from the cornea (to provide a corneal reflex) in the video image (provided by CCD camera 2304), one can determine the position of the visual axis of eye 2107 relative to the position of the beam of scanning OCT radiation (in accordance with any one of a number of methods that are well known to those of ordinary skill in the art).

It should be clear to those of ordinary skill in the art that the apparatus to provide a video path and/or a corneal reflex described above in conjunction with FIG. 5 may be used to provide the same for the embodiment described above in conjunction with FIG. 4. Further, it should be clear to those of ordinary skill in the art that the embodiments described above in conjunction with FIGS. 4 and 5 may also be used with the ophthalmologic microscope described above in conjunction with FIG. 2.

Those skilled in the art will recognize that the foregoing description has been presented for the sake of illustration and description only. As such, it is not intended to be exhaustive or to limit the invention to the precise form disclosed. For example, the above-described embodiments may also be used to scan any portion of features of an eye. In particular, in accordance with one such embodiment, the scanning system may be adjusted so that its image surface more closely resembles a particular segment of a scanned feature.

What is claimed is:

1. A scanner for a beam of scanning optical coherence tomography ("OCT") radiation that comprises:

a source of OCT radiation;

a scanner; and scanning optics whose image surface has a negative field curvature.

2. The scanner of claim 1 wherein the scanning optics comprises:

at least two spaced-apart lens elements.

3. The scanner of claim 2 wherein the at least two spaced-apart lens elements include a positive lens elements that is spaced-apart from a negative lens element.

4. The scanner of claim 3 wherein the positive lens element is fabricated from a first type of material and the negative lens element is fabricated from a second type of material.

5. The scanner of claim 1 wherein the shapes of the positive lens element and the negative lens element are designed to correct for one or more types of optical aberration.

6. The scanner of claim 4 wherein the positive lens element and the negative lens element are an achromat.

7. The scanner of claim 6 wherein the achromat is a dialyte.

8. The scanner of claim 1 wherein a distance between the scanner and the scanning system is about one focal length of the scanning system.

9. The scanner of claim 1 which further comprises an optometer that images an object on an eye.

10. The scanner of claim 9 wherein the optometer comprises:

a target lens system, wherein the object is disposed substantially at a back focal plane of the target lens system;

a negative lens system disposed after the target lens system; and a collimating lens system disposed between the negative lens system and the eye.

11. The scanner of claim 10 wherein a position of the negative lens system is adjustable along an optic axis of the optometer.

12. The scanner of claim 11 wherein a pupil of the eye is positioned substantially at a front focal plane of the collimating lens system.

13. The scanner of claim 9 wherein the object is movable along an optic axis of the optometer and wherein the scanner further comprises:

a radiation source and a lens system disposed to image radiation output from the radiation source onto the eye; and a video lens system and a beamdirector to form a real image of the radiation output that is reflected from the eye on a camera.

14. An OCT scanning apparatus that comprises:

an optical coherence tomography ("OCT") apparatus that outputs a beam of OCT radiation;

a scanner that raster scans the beam of OCT radiation;

scanning optics whose image surface has a negative field curvature that couples the scanned beam of OCT radiation onto an object; and an analyzer;

wherein the OCT apparatus generates detection signals in response to reflected and scattered OCT radiation collected from the object; and wherein the analyzer analyzes the detected signals to provide an OCT image.

15. The OCT scanning apparatus of claim 3 which further comprises an ophthalmologic microscope.

* * * * *